United States Patent
Ito et al.

(10) Patent No.: US 7,959,558 B2
(45) Date of Patent: Jun. 14, 2011

(54) CAMERA HEAD FOR ENDOSCOPE, CAMERA SYSTEM FOR ENDOSCOPE, AND ENDOSCOPE SYSTEM

(75) Inventors: Mitsuhiro Ito, Tokyo (JP); Junichi Ohnishi, Tokyo (JP); Hiroyuki Kuroda, Tokyo (JP)

(73) Assignee: Olympus Corporation, Tokyo (JP)

( * ) Notice: Subject to any disclaimer, the term of this patent is extended or adjusted under 35 U.S.C. 154(b) by 1216 days.

(21) Appl. No.: 11/639,176

(22) Filed: Dec. 14, 2006

(65) Prior Publication Data

US 2007/0088196 A1 Apr. 19, 2007

Related U.S. Application Data

(63) Continuation of application No. PCT/JP2005/007440, filed on Apr. 19, 2005.

(30) Foreign Application Priority Data

Jun. 16, 2004 (JP) ................................ P2004-178152

(51) Int. Cl.
*A61B 1/04* (2006.01)
*H04N 7/18* (2006.01)

(52) U.S. Cl. ........................... 600/112; 348/73; 600/109
(58) Field of Classification Search .................. 600/112, 600/109–110; 348/73–75
See application file for complete search history.

(56) References Cited

U.S. PATENT DOCUMENTS

| | | | |
|---|---|---|---|
| 4,413,278 A * | 11/1983 | Feinbloom | 348/73 |
| 4,639,772 A | 1/1987 | Sluyter | |
| 4,797,737 A * | 1/1989 | Yazawa | 348/73 |
| 5,010,876 A * | 4/1991 | Henley et al. | 600/112 |
| 5,609,561 A * | 3/1997 | Uehara et al. | 600/112 |
| 5,868,664 A | 2/1999 | Speier et al. | |
| 5,879,289 A | 3/1999 | Yarush et al. | |
| 5,986,693 A * | 11/1999 | Adair et al. | 348/76 |
| 6,310,642 B1 | 10/2001 | Adair et al. | |
| 6,432,046 B1 | 8/2002 | Yarsuh et al. | |
| 2002/0022763 A1 | 2/2002 | Sano et al. | |
| 2002/0101507 A1 * | 8/2002 | Saito et al. | 348/65 |

FOREIGN PATENT DOCUMENTS

| | | |
|---|---|---|
| CN | 2467047 Y | 12/2001 |
| JP | 7-39515 | 2/1995 |
| JP | 2000-116599 | 4/2000 |
| JP | 2003-198894 | 7/2003 |

* cited by examiner

*Primary Examiner* — Philip R Smith
(74) *Attorney, Agent, or Firm* — Scully, Scott, Murphy & Presser, P.C.

(57) ABSTRACT

In a camera head for an endoscope, a camera system for an endoscope, and an endoscope system of the invention, a camera head section has: an adaptor connection section to be connected to an eyepiece section of an endoscope that enables observation of inside of a body cavity of a subject; a CCD which picks up an observation image from the eyepiece section connected by the adaptor connection section; an image signal processing device which processes an image signal of the observation image picked up by the CCD; a cable including a connector as an output device which outputs the image signal from the image signal processing device; and a recording device which records the image signal.

6 Claims, 2 Drawing Sheets

CAMERA HEAD FOR ENDOSCOPE, CAMERA SYSTEM FOR ENDOSCOPE, AND ENDOSCOPE SYSTEM

PRIORITY CLAIM

This application is continuation application of a PCT Application No. PCT/JP2005/007440, filed on Apr. 19, 2005, entitled "CAMERA HEAD FOR ENDOSCOPE, CAMERA SYSTEM FOR ENDOSCOPE, AND ENDOSCOPE SYSTEM" whose priority is claimed on Japanese Patent Application No. 2004-178152, filed on Jun. 16, 2004. The description thereof is incorporated herein by reference.

BACKGROUND OF THE INVENTION

1. Field of the Invention

The present invention relates to a camera head for an endoscope, a camera system for an endoscope, and an endoscope system that enable image pickup of an observation image from an endoscope by a provided image pickup device.

2. Description of Related Art

Recently, an optical type endoscope has been widely used. In general, an observation image is observed from an eyepiece section with the unassisted eye when using such an endoscope. However, in some cases, it is used as an endoscope system in which a camera head having a built-in image pickup device is attached to the eyepiece section and is able to display a picked up observation image (image) on a TV camera or record the image on a video device or the like (see, for example, Japanese Unexamined Patent Application, First Publication, No. H07-39515). In such cases, the image signal is transmitted from the image pickup device provided on the camera head through a cable to an external CCU (camera control unit), and after having processed the image signal in the CCU, the image signal is transmitted to an external TV camera or video device to carry out display or recording.

In the case where a desired image is displayed or recorded using an endoscope system of such a configuration, an image signal to which image signal processing has been applied, that is, an image signal from the CCU needs to be transmitted to a TV camera, or video device. As a result, the image signal is transmitted to an external device separated from the endoscope, and is displayed or recorded after being subjected to image signal processing.

SUMMARY OF THE INVENTION

A camera head for an endoscope according to the present invention includes: a connection device to be connected directly or via a connection adaptor to an eyepiece section of an endoscope that enables observation of inside of a body cavity of a subject; an image pickup device which picks up an observation image from the eyepiece section connected by the connection device; an image signal processing device which processes an image signal of the observation image picked up by the image pickup device; an output device which outputs the image signal from the image signal processing device; and a recording device which records the image signal.

Moreover, the camera system for an endoscope according to another aspect of the present invention includes: the camera head for an endoscope; an input device that is a separate body from the camera head for an endoscope and that is removably connected to the output device to input the image signal; and a display device integrally provided with an image display device which converts the image signal to an image and displays the image signal.

Furthermore, the endoscope system according to another aspect of the present invention includes: an endoscope having an eyepiece section that enables observation of the inside of a body cavity of a subject; and the camera system for an endoscope.

DETAILED DESCRIPTION OF THE INVENTION

Figure 1:
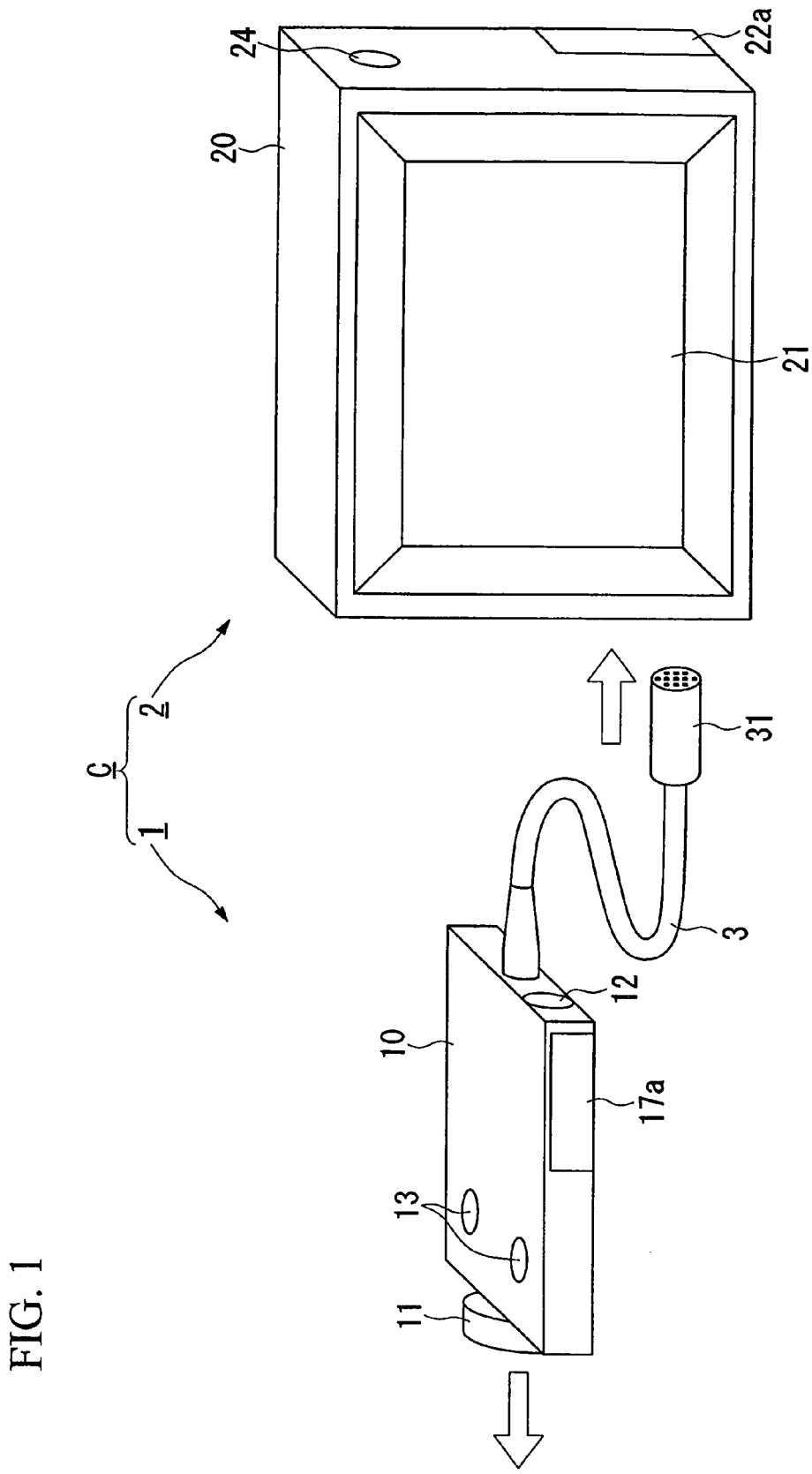
FIG. 1 is a schematic block diagram that shows a camera for an endoscope and a camera system for an endoscope according to a first embodiment of the present invention.
Figure 2:
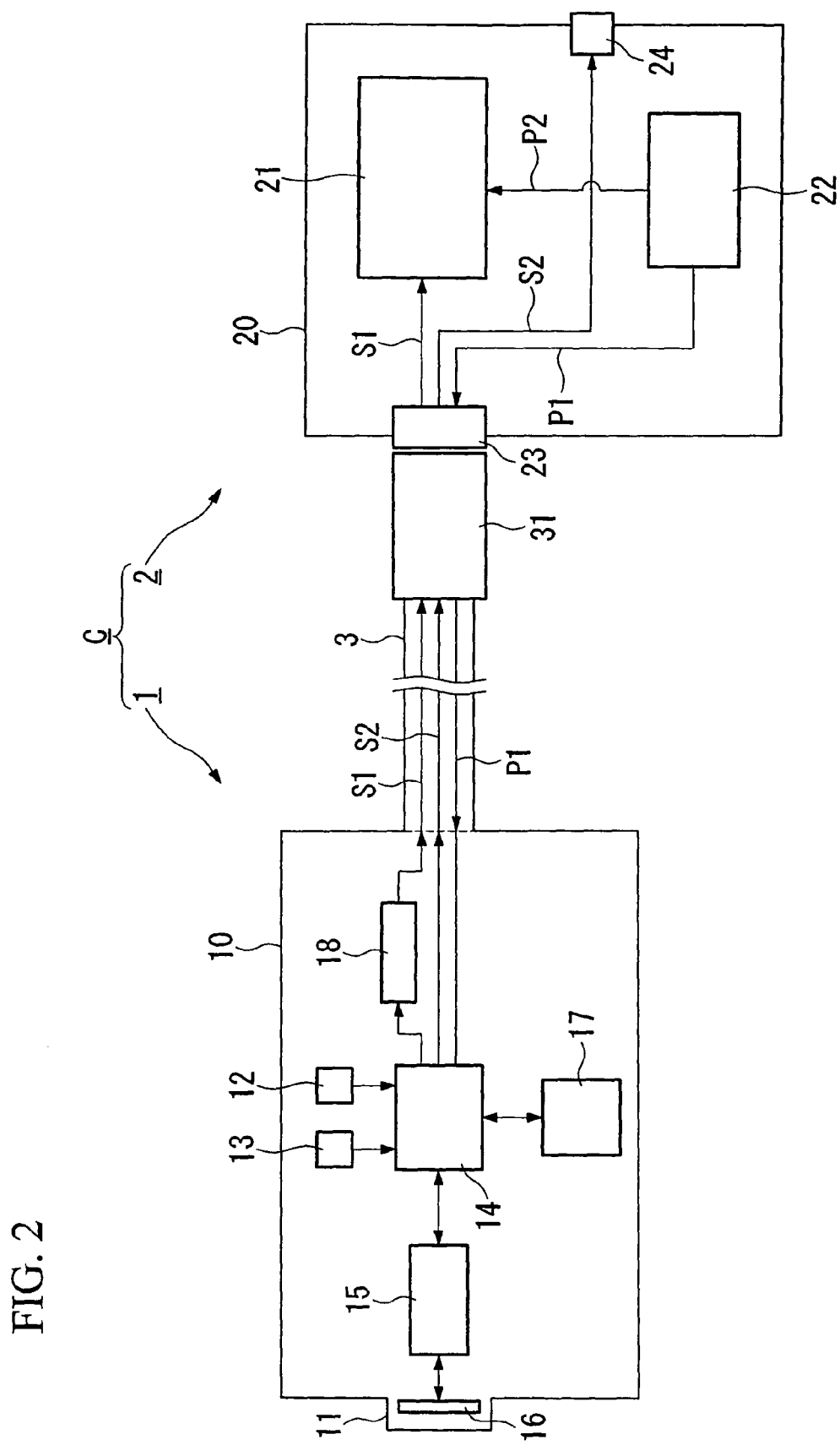
FIG. 2 is a block diagram that shows the camera for an endoscope and the camera system for an endoscope according to the first embodiment of the present invention shown in FIG. 1.

Hereinafter, an embodiment of the present invention is described, with reference to FIG. 1 and FIG. 2.

A camera system C for an endoscope according to the present invention is configured with a camera head section (camera head for endoscope) 1 and a display device section (display device) 2 that can be detached from each other. By combining this camera system C for an endoscope with an endoscope having an eyepiece section for enabling observation of body cavity of a patient (subject), an endoscope system that can process (image signal processing), record, and display an image from the endoscope can be configured.

The camera head section 1 has an adaptor connection section (connection device) 11 and a cable (output device) 3 provided integrally with a first casing 10, which is a base body of the camera head section 1.

The adaptor connection section 11 is provided so as to project from a tip end side of the first casing 10, and is for connecting to an eyepiece section of an endoscope via a connection adaptor (not shown in the drawings). The camera head section 1 is integrally attached to the eyepiece section of the endoscope by this adaptor connection section 11. An observation image (image) from the eyepiece section is imaged through the adaptor connection section 11 onto a CCD (Charge Coupled Device) 16 that serves as an image pickup device (described later).

Here, a connection device for connecting to the eyepiece of the endoscope is configured to connect via the adaptor connection section 11 as a connection adaptor. However, the connection device may be configured to be able to connect to the eyepiece directly. In this case, the connection device may be made to have a shape and structure that conforms to certain types or models of endoscopes so that the connection adaptor is not required.

A power switch 12 and a control switch 13 are installed in the first casing 10 and a recording medium slot section 17a for inserting and removing a recording device 17 to be described later (for example, a memory card) into and from the first casing 10 is formed in the first casing 10. Moreover, as shown in FIG. 2, the first casing 10 has an image signal processing device 14 (for example, an ASIC (Application Specific Integrated Circuit)), an AFE/TG (analog front end/timing generator) 15, the CCD 16, the recording device 17, and an LCD driver 18 built therein.

The power switch 12 turns a power supply of the camera system C for an endoscope on and off. Moreover, in addition to a release switch function for picking up an observation image on the CCD 16, the control switch 13 also has a recording switch function for recording an image signal from the image signal processing device 14 to the recording device 17 and so forth.

The image signal processing device 14 is a control circuit substrate, which serves as a CCU (camera control unit), for performing overall control of the operation of the camera system C for an endoscope. That is to say, turning the power supply on and off, observation image pickup, or image signal processing and so forth are all performed by this image signal processing device 14.

The CCD 16 picks up an observation image from the eyepiece section and processes it into an image signal to be outputted. The CCD 16 is connected to the image signal processing device 14 via the AFE/TG (analog front end/timing generator) 15. The AFE/TG 15 transmits a predetermined pulse signal for driving the CCD 16 and performs A/D conversion (analog/digital conversion) of an analog image signal transmitted from the CCD 16 then digitizes the image signal and transmits it to the image signal processing device 14.

The recording device 17 is a card type recording medium (memory card) such as a XD card (product name), and it records the image signal transmitted from the image signal processing device 14. This recording device 17 can be attached to and removed from the camera head section 1 by being inserted into and removed from the recording medium slot section 17a shown in FIG. 1. That is, since the recording device 17 can be detached from the camera head section 1 after an image has been recorded thereon, this recording device 17 can easily be attached to an external device to observe the image on the external device, or data of the image can be easily recorded onto another recording device.

The LCD driver 18 amplifies the image signal outputted from the image signal processing device 14, and is provided part way along a transmission path of a first signal line S1, which is described later, between the image signal processing device 14 and the cable 3. Since the image signal from the image signal processing device 14 is transmitted to the display device section 2 through the cable 3 as is described later, by amplifying the image signal using the LCD driver 18, degradation in the image signal can be suitably suppressed during transmission through the cable 3.

A base end side of the cable 3 is integrally attached to the first casing 10, and on a tip end side of the cable 3 there is provided a connector (output device) 31 to which a connector (input device) 23 (described later) provided in the display device section 2 is removably connected. By connecting the connector 31 and the connector 23, the camera head section 1 and the display device section 2 are integrally joined and are electrically connected.

The display device section 2 is of a configuration integrally provided with a LCD 21 as a display device, a battery 22, a connector 23, and a video output terminal 24 to which a video recording device or the like can be connected, within a second casing 20 that forms a separate body from the first casing 10 and that is a base body of the display device section 2. Moreover, a battery slot 22a for inserting and removing the battery 22 into and from the second casing 20 is formed in the second casing 20.

When the connector 31 and the connector 23 are connected, that is, when the camera system C for an endoscope is set up by joining the camera head section 1 and the display device section 2, a power supply line P1, the first signal line S1, and a second signal line S2 are respectively formed between the camera head section 1 and the display device section 2 through the connector 31 and the connector 23. The power supply line P1 supplies electric power from the battery 22 to the image signal processing device 14. The electric power supplied to the image signal processing device 14 through this power supply line P1 is supplied to the respective components within the camera head section 1. The first signal line S1 transmits the image signal output, after this output has been subjected to a predetermined image signal processing in the image signal processing device 14, to the LCD 21. The second signal line S2 transmits the image signal output, after this output has been subjected to a predetermined image signal processing in the image signal processing device 14, to the video output terminal 24.

Furthermore, power supply from the battery 22 to the LCD 21 is carried out through a power supply line P2 formed within the display device section 2.

Thus, since comparatively heavy weight components such the LCD 21 and battery 22 are provided within the display device section 2, which is a separate body from the camera head section 1, significant reduction in size and weight of the camera head section 1 can be achieved. Since the display device section 2 can be detached from the camera head section 1, sterilization processes such as EOG (gas sterilization) need be applied only to the downsized light-weight camera head section 1, and sterilization, including sterilizing of the cable 3, can be precisely carried out in a short period of time. That is to say, since the display device section 2 is to be placed in a position distanced from the patient by 1 to 2 m via the cable 3, it does not require a sterilization process to be carried out especially.

When using the camera system C for an endoscope configured as described above, the camera head section 1 is integrally attached to the eyepiece section of an endoscope via the connection adaptor, and the connector 31 is connected to the connector 23 of the display device section 2 with the endoscope in a state of being inserted into the patient's body cavity. Then, the camera system C for an endoscope is operated by operating the power switch 12 and the control switch 13.

An observation image (image) from the eyepiece section picked up by the CCD 16 is transmitted as an analog image signal to the AFE/TG 15, and after having been A/D converted, it is transmitted as a digital image signal to the image signal processing device 14. Predetermined image signal processes such as color correction are applied to this image signal in the image signal processing device 14. The term color correction here refers to color correction that enhances and produces red color, and not to color correction that produces three colors of red, blue and green equally as in a general electrical camera (digital camera). By enhancing the red color in this way, distinction of the colors of organs can be easily made and bleeding, tumor, or lesions in organs can be accurately discovered in a short period of time. In other words, the image signal processing device 14 performs color correction suitable for observing an image of inside a body cavity.

The image signal to which image signal processing including such color correction has been applied is transmitted to the first signal line S1 and the second signal line S2, and is transmitted to the recording device 17 to be recorded. The image signal transmitted to the first signal line S1 is amplified by the LCD driver 18 partway along the transmission path before being outputted to the connector 23 through the cable 3, and is converted into an image to be displayed on the LCD 21. Moreover, the image signal transmitted to the second signal line S2 is outputted to the connector 23 through the cable 3, and is transmitted to the video output terminal 24. If an external video recording device or the like is connected to this video output terminal 24, then images from the CCD 16 can be video recorded.

The camera head section 1 according to the present embodiment is provided with: the adaptor connection section 11 to be connected via the connection adaptor to the eyepiece section of the endoscope that enables observation of the inside of a patient's body cavity; the CCD 16 that picks up an observation image from the eyepiece section connected by the adaptor connection section 11; the image signal processing device 14 that serves as an image signal processing device for image signal processing an observation image picked up by the CCD 16; the cable 3 including the connector 31 that serves as an output device for outputting the image signal from the image signal processing device 14; and the recording device 17 for recording the image signal.

Accordingly, picking up an observation image from the eyepiece of the endoscope, and also a series of operations including image signal processing, recording, and output can be performed in the camera head section 1. As a result, image signal processing and recording can be easily and accurately carried out providing a high level of manageability and convenience.

Furthermore, the camera system C for an endoscope according to the present embodiment is provided with: the camera head section 1; and the display device section 2 that is a separate body from the camera head section 1, integrally furnished with the LCD 21 that converts the image signal into an image and displays the image, and the connector 23 that serves as an input device to be removably connected to the connector 31 of the cable 3 to input the image signal.

As described above, since the display device section 2 and the camera head section 1 are separate bodies, a reduction in size and weight of the camera head 1 for an endoscope can be achieved, and since an image can be displayed and observed on the display device section 2 as necessary, image recording and image display can be easily and accurately carried out, improving the level of manageability and convenience.

Furthermore, if an endoscope having an eyepiece that enables observation of inside of patient's body cavity is combined with the camera system C for an endoscope, an endoscope system that enables image pick up, image signal processing, recording, and display can be provided as a small scale device configuration.

Moreover, in the embodiment described above, the battery is to be provided only within the display device section, however, a small sized battery may be provided within the camera head section. By so doing, then even in the case where the image does not need to be displayed, that is, when the display device section has been detached, image pick up, image signal processing, and recording can still be carried out.

Moreover, the camera head section and the display device section are connected by wire. However, the configuration may be such that communication sections that enable wireless communication are respectively provided within the camera head section and the display device section to carry out wireless data transmission and reception via these communication sections.

In the camera head for the endoscope as described above, picking up an observation image from the eyepiece of the endoscope, and also a series of operations including image signal processing, recording, and output can be carried out in the camera head section.

Since the display device and the camera head for an endoscope are separate bodies as described above, a reduction in the size and weight of the camera head for an endoscope can be achieved, and the image can be displayed and observed as needed.

As described above, the present invention can provide the camera head for the endoscope that enables easy and accurate processing and recording of an image signal and that has a high level of manageability and convenience, and a camera system for an endoscope and an endoscope system that have the aforementioned camera head and are able to display an image.

The preferred embodiment of the present invention has been described. However, the present invention is not limited to the embodiment. Addition, omission, replacement or other types of modification may be made to the configuration without departing from the scope of the present invention. The present invention is not to be limited by the description above and is to be limited only by the scope of claims attached.

The camera head for an endoscope, the camera system for an endoscope, and the endoscope system of the present invention can be utilized not only for medical applications but can also be suitably used for industrial applications.

What is claimed is:

1. A camera system for an endoscope the camera system comprising:
    a camera head including:
        a connection device to be connected directly or via a connection adaptor to an eyepiece section of an endoscope that enables observation of inside of a body cavity of a subject;
        an image pickup device which picks up an observation image from said eyepiece section connected by said connection device;
        an image signal processing device which processes an image signal of the observation image picked up by said image pickup device;
        an output device which outputs the image signal from said image signal processing device;
        a recording device which records the image signal;
        a first casing which accommodates said image pickup device, said image signal processing device, said output device and said recording device, and has a recording medium slot section which ejects said recording device from said first casing; and
    a display device comprising:
        an input device that is connected to said output device and is disconnectable from said output device;
        an image display device which receives the image signal outputted from said output device via said input device, converts the image signal to an image and displays the image; and
        a second casing which is a separate casing from said first casing, and accommodates said input device and said image display device;
    wherein said display device further comprises a battery which supplies electric power to said image signal processing device via said input device and said output device, and said second casing accommodates said battery.

2. An endoscope system comprising:

an endoscope having an eyepiece section that enables observation of the inside of a body cavity of a subject; and the camera system for an endoscope according to claim 1.

3. The camera system for an endoscope according to claim 1, wherein said recording device is a card type recording medium.

4. The camera system for an endoscope according to claim 1, wherein said second casing has a battery slot which ejects said battery from said second casing.

5. The camera system for an endoscope according to claim 1, wherein said battery supplies electric power to said image display device.

6. The camera system for an endoscope according to claim 1, wherein said display device is placed in a position distanced from the subject by approximately 1 to 2 meters via a cable.

* * * * *